US00PP17878P2

(12) United States Plant Patent
Danziger

(10) Patent No.: US PP17,878 P2
(45) Date of Patent: Jul. 24, 2007

(54) ***TORENIA* PLANT NAMED 'DANCAT911'**

(50) Latin Name: *Torenia hybrida*
Varietal Denomination: Dancat911

(75) Inventor: Gabriel Danziger, Moshav Nir Zvi (IL)

(73) Assignee: Danziger "Dan" Flower Farm, Post Beit Dagan, IL (US)

( * ) Notice: Subject to any disclaimer, the term of this patent is extended or adjusted under 35 U.S.C. 154(b) by 0 days.

(21) Appl. No.: 11/351,845

(22) Filed: Feb. 10, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Torenia* plant named 'Dancat911', characterized by its upright, outwardly spreading to cascading, and uniformly mounded plant habit; freely branching and vigorous growth habit; shiny dark-green colored foliage; early, freely and continuous flowering habit; light blue purple-colored flowers; and good garden performance.

1 Drawing Sheet

Botanical designation: *Torenia hybrida.*
Cultivar denomination: 'Dancat911'.

BACKGROUND OF THE INVENTION

The present Invention relates to a new and distinct cultivar of *Torenia* plant, botanically known as *Torenia hybrida,* and hereinafter referred to by the cultivar name Dancat911.

The new *Torenia* is a naturally-occurring whole plant mutation of the *Torenia hybrida* cultivar Dantopur, disclosed in U.S. Plant Pat. No. 13,723. The new *Torenia* was discovered and selected by the Inventor in February, 2002 in a controlled environment in Moshav Mishmar Hashiva, Israel.

Asexual reproduction of the new cultivar by terminal cuttings at Moshav Mishmar Hashiva, Israel since April, 2002, has shown that the unique features of this new *Torenia* are stable and reproduced true to type in successive generations.

SUMMARY OF THE INVENTION

Plants of the cultivar Dancat911 have not been observed under all possible environmental conditions. The phenotype may vary somewhat with variations in environment such as temperature and light level without, however, any variance in genotype.

The following traits have been repeatedly observed and are determined to be the unique characteristics of 'Dancat911'. These characteristics in combination distinguish 'Dancat911' as a new and distinct cultivar of *Torenia:*

1. Upright, outwardly spreading to cascading, and uniformly mounded plant habit.
2. Freely branching and vigorous growth habit.
3. Shiny dark-green colored foliage.
4. Early, freely and continuous flowering habit.
5. Light blue purple-colored flowers.
6. Good garden performance.

Plants of the new *Torenia* can be compared to plants of the parent, the cultivar Dantopur. In side-by-side comparisons conducted in Moshav Mishmar Hashiva, Israel, plants of the new *Torenia* differed from plants of the cultivar Dantopur in the following characteristics:

1. Plants of the new *Torenia* were bushier than plants of the cultivar Dantopur.
2. Plants of the new *Torenia* had smaller flowers than plants of the cultivar Dantopur.

Plants of the new *Torenia* can be compared to plants of the cultivar Dantopinkmn, disclosed in U.S. Plant Pat. No. 16,011. In side-by-side comparisons conducted in Moshav Mishmar Hashiva, Israel, plants of the new *Torenia* differed from plants of the cultivar Dantopinkmn in the following characteristics:

1. Plants of the new *Torenia* were bushier than plants of the cultivar Dantopinkmn.
2. Plants of the new *Torenia* and the cultivar Dantopinkmn differed in flower color as plants of the cultivar Dantopinkmn had pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Torenia.*

The photograph at the bottom of the sheet is a side perspective view of a typical plant of 'Dancat911'.

The photograph at the top of the sheet is a close-up view of typical flowers and leaves of 'Dancat911'.

DETAILED BOTANICAL DESCRIPTION

The aforementioned photographs and following observations and measurements describe plants grown in Bonsall, Calif., in a polyethylene-covered greenhouse during the winter with day temperatures ranging from 18° C. to 32° C. and night temperatures ranging from 13° C. to 21° C. Plants were grown in 15-cm containers and were about four months old when the photographs and description were taken. Color references are made to The Royal Horticultural Society Colour Chart, 1995 Edition, except where general terms of ordinary dictionary significance are used.

Botanical classification: *Torenia hybrida* cultivar Dancat911.

Parentage: Naturally-occurring whole plant mutation of *Torenia hybrida* cultivar Dantopur, disclosed in U.S. Plant Pat. No. 13,723.

Propagation:

*Type.*—By terminal cuttings.

*Time to initiate roots, summer.*—About seven days at 24° C.

*Time to initiate roots, winter.*—About ten days at 18° C.

*Time to produce a rooted plant, summer.*—About 18 to 25 days at 24° C.

*Time to produce a rooted plant, winter.*—About 25 to 30 days at 18° C.

*Root description.*—Fine and fibrous.

*Rooting habit.*—Freely branching.

Plant description:

*Plant form/habit.*—Upright, outwardly spreading to cascading, and mounded plant habit; broadly inverted triangle; vigorous growth habit. Freely branching habit; dense and bushy growth habit.

*Plant height.*—About 18 cm.

*Plant width* (*spread*).—About 48.5 cm.

*Lateral branches.*—Quantity per plant: Freely branching habit, about six primary lateral branches each with numerous secondary lateral branches. Length: About 38 cm. Diameter: About 3 cm. Internode length: About 6.5 cm. Strength: Strong, but cascading. Texture: Smooth, glabrous. Color: 145A.

*Foliage description.*—Arrangement: Opposite, simple. Length: About 5 cm. Width: About 3.7 cm. Shape: Ovate. Apex: Broadly acute. Base: Cordate. Margin: Serrate. Texture, upper and lower surfaces: Smooth, glabrous. Venation pattern: Pinnate; arcuate. Color: Developing and fully expanded leaves, upper surface: 147A; venation, 147B; shiny. Developing and fully expanded leaves, lower surface: 147B; venation, 147C. Petiole length: About 1.2 cm. Petiole diameter: About 2 mm. Petiole texture, upper and lower surfaces: Sparsely pubescent. Petiole color, upper and lower surfaces: 146B.

Flower description:

*Flower type/habit.*—Single flowers with bilabiate corolla and tubular calyx; flowers face mostly outward. Freely flowering habit with about 42 flower buds and open flowers per lateral branch.

*Fragrance.*—None detected.

*Natural flowering season.*—Flowers begin flowering about four to six weeks after planting and flower continuously under greenhouse conditions. Flowers not persistent.

*Postproduction longevity.*—Flowers last about five to seven days on the plant.

*Flower buds.*—Height: About 2.2 cm. Diameter: About 7 mm. Shape: Obovate to elongate. Color: 144A.

*Flowers.*—Diameter: About 2.5 cm by 2.8 cm. Depth: About 2.8 cm.

*Petals.*—Quantity per flower: Typically four in a single whorl; petals fused at the base. Lobe length, upper and lower petals: About 1.2 cm. Lobe length, lateral petals: About 8 mm. Lobe width, upper petal: About 1.8 cm. Lobe width, lateral petals: About 1.9 cm. Lobe width, lower petal: About 1.4 cm. Shape: Oval. Apex: Rounded. Margin, upper petal: Sinuate. Margin, lateral and lower petals: Entire. Texture, upper and lower surfaces: Smooth, glabrous; satiny. Color: Developing petals, upper surface: Upper petal: 92D. Lateral petals: 93A. Lower petal: 89B. Developing, lower surface: Upper petal: 92D. Lateral petals: 93B. Lower petal: 92B. Fully expanded petals, upper surface: Upper petal: 92C; towards the margin, 89B. Lateral petals: 92C; towards the margins, 93A. Lower petal: 92C; towards the margin, 93C; spot, 12A. Fully expanded petals, lower surface: Upper petal: 92C; towards the margin, 92A. Lateral petals: 93B. Lower petal: 92D; towards the margin, 92B. Throat: 92C. Tube: 92B to 92C.

*Sepals.*—Quantity per flower: Five, fused; tubular bi-lobed calyx. Calyx length: About 1.7 mm. Calyx diameter: About 9 mm. Shape: Elliptic. Apex: Acute. Margin: Entire. Texture, upper and lower surfaces: Smooth, glabrous. Color, immature and mature, upper surface: 144B. Color, immature and mature, lower surface: 144A.

*Peduncles.*—Length: About 8 mm. Diameter: About 2 mm. Texture: Smooth, glabrous. Angle: About 35° to 45° from stem axis. Color: 46C.

*Reproductive organs.*—Stamens: Quantity per flower: Typically four. Anther shape: Oblong. Anther size: About 3 mm by 1 mm. Anther color: 90A. Pollen amount: Scarce. Pollen color: 155A. Pistils: Quantity per flower: Typically one. Pistil length: About 2.2 cm. Style length: About 2 cm. Style color: 155D. Stigma shape: Anvil-shaped, flattened. Stigma color: 155D. Ovary color: 144A.

*Seed/fruit.*—Seed and fruit development have not been observed.

Disease/pest resistance: Plants of the new *Torenia* have not been observed to be resistant to pathogens or pests common to *Torenia*.

Garden performance: Plants of the new *Torenia* have been observed to have good garden performance and tolerate rain, wind and temperatures from 5° C. to 35° C.

It is claimed:

1. A new and distinct cultivar of *Torenia* plant named 'Dancat911', as illustrated and described.

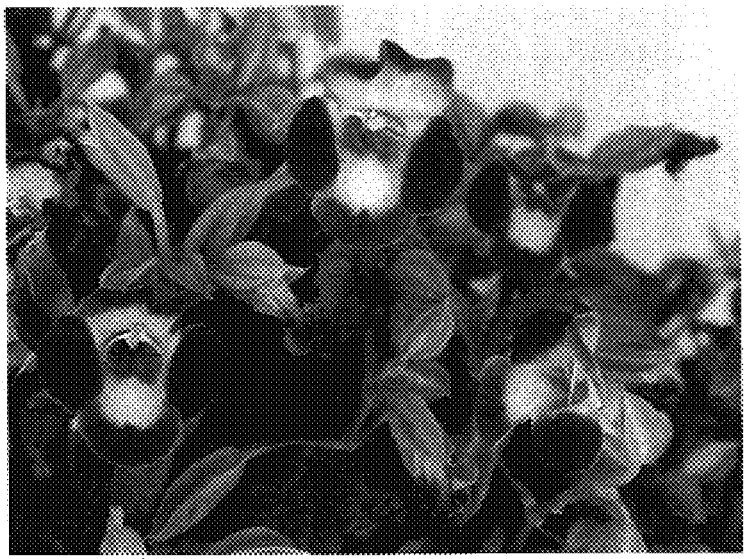
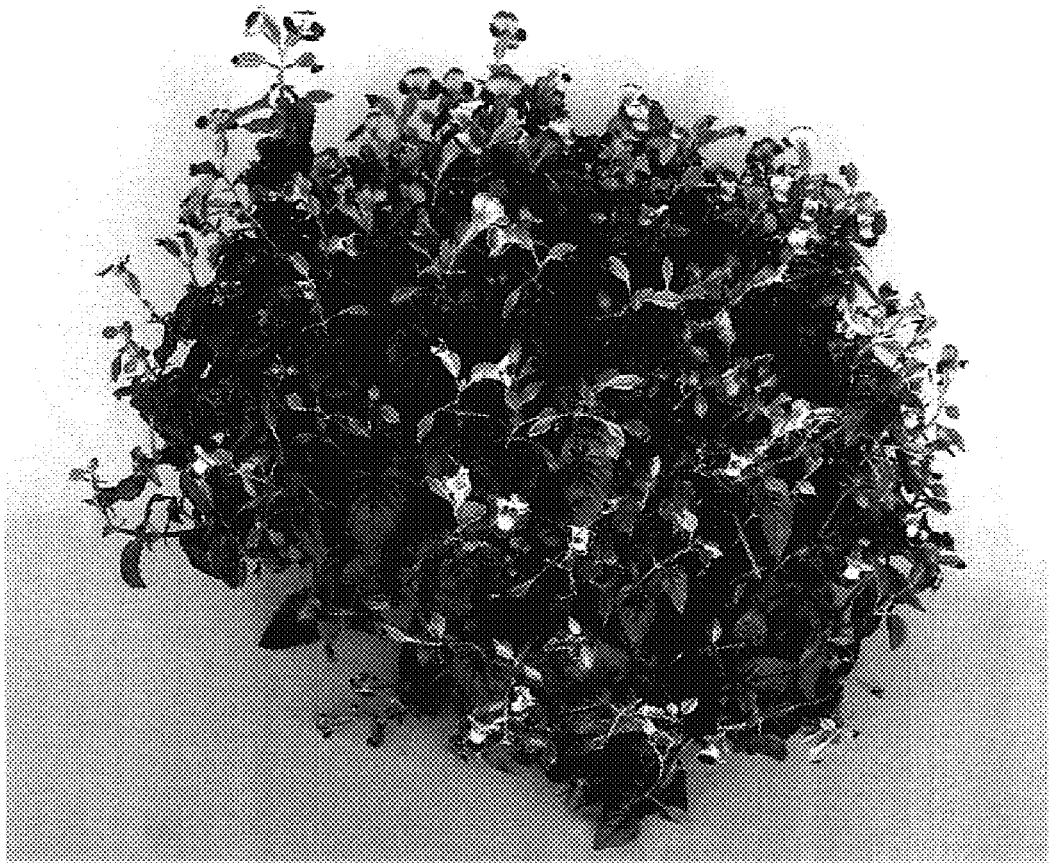

* * * * *